United States Patent [19]

Maslanka

[11] Patent Number: 4,467,802
[45] Date of Patent: Aug. 28, 1984

[54] SURGICAL GRIPPING INSTRUMENT

[76] Inventor: Harald Maslanka, Im jungen Steigle 6, D-7200 Tuttlingen, Fed. Rep. of Germany

[21] Appl. No.: 343,202

[22] Filed: Jan. 27, 1982

[30] Foreign Application Priority Data

Mar. 31, 1980 [DE] Fed. Rep. of Germany ....... 3012447

[51] Int. Cl.³ .............................................. A61B 17/28
[52] U.S. Cl. .................................. 128/321; 128/354; 128/356; 294/99 S
[58] Field of Search ............................... 128/321–324, 128/354, 356, 749, 751, 303 R; 294/99 S, 100, 114

[56] References Cited

U.S. PATENT DOCUMENTS

| 1,963,636 | 6/1934 | Wappler | 128/303.15 |
| 2,137,710 | 11/1938 | Anderson | 128/321 |
| 4,174,715 | 11/1979 | Hasson | 128/321 |
| 4,393,872 | 7/1983 | Reznik et al. | 128/321 X |

FOREIGN PATENT DOCUMENTS

| 123563 | 6/1931 | Austria | 128/321 |
| 2454371 | 6/1975 | Fed. Rep. of Germany | 128/321 |
| 2735706 | 2/1978 | Fed. Rep. of Germany | . |

OTHER PUBLICATIONS

"HM" Flexible PE-Zangen zur Brocho-, Bulbo-, Colo-, Duodeno-, Endo- und Gastrokopie; Harald Maslanka, author.

Primary Examiner—Dalton L. Truluck
Attorney, Agent, or Firm—Wood, Dalton, Phillips, Mason & Rowe

[57] ABSTRACT

A gripping instrument particularly for surgical application. A sheathed cable is associated with separate thumb and finger holds. The finger hold has a first fixed rack meshing with a pinion on a shaft associated with the thumb hold to which a cable core end is fixed. A second rack fixedly engages the cable sheath. In operation the finger hold is drawn towards the thumb hold, shifting the racks axially oppositely. In so doing the sheath is extended over a split end of the cable core drawing the free ends together in tong-like fashion without axially shifting the gripping ends.

6 Claims, 1 Drawing Figure

U.S. Patent
Aug. 28, 1984
4,467,802
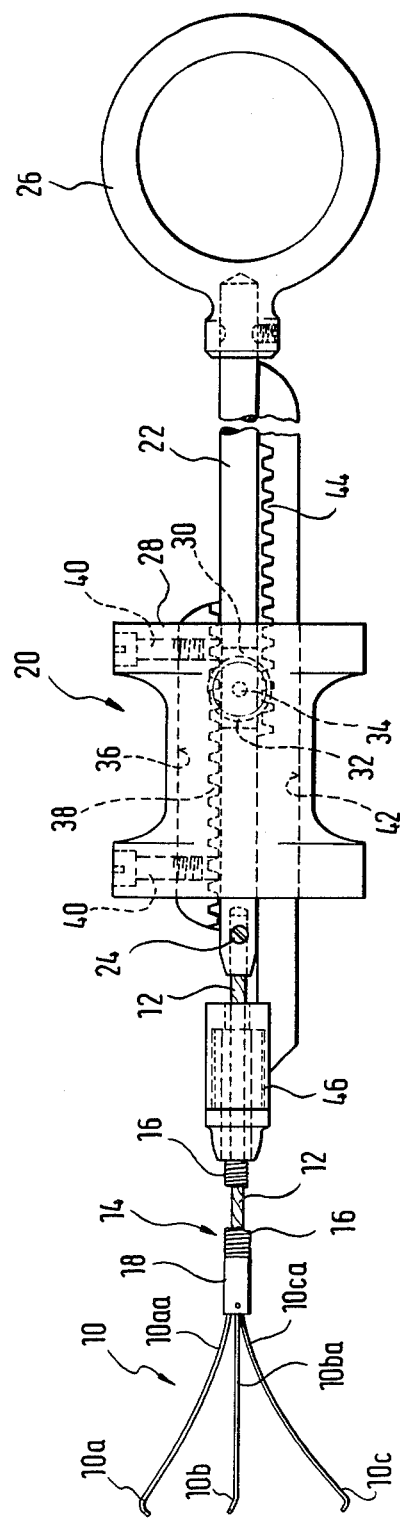

SURGICAL GRIPPING INSTRUMENT

BACKGROUND OF THE INVENTION

1. Field of the Invention

The invention relates to a surgical gripping instrument to be introduced into body cavities.

2. Background Art

Surgical gripping instruments are well known in the art. An exemplary structure is one including a manual operating device associated with a transmission cable having a cable sheathing and a cable core. Gripping elements are coupled to the end of the cable core on the patient's side. The gripping elements have connection parts controlled by the end of the cable sheathing on the patient's side which is movable relative to the cable core or by an end sleeve connected with the operating end of the cable sheathing. The end of the cable sheathing is connected with a finger hold of the manual operating device and the cable core connected with a thumb hold of the manual operating device. The thumb and finger holds are movable relative to each other to effect relative motion of the cable sheathing and cable core.

Such a surgical gripping instrument is used especially for the purposes of bronchoscopy, bulboscopy, coloscopy, duodenoscopy, endoscopy and gastroscopy.

In a surgical gripping instrument of the type described, a thumb hold is connected with the end of the cable sheathing on the operating side and an index finger-middle finger hold is connected with the end of the cable core on the operating side. If the handling physician or the surgical nurse bring the index finger-middle finger hold closer to the thumb hold, the core is retracted relative to the cable sheathing on the patient's side and the connection parts of the gripping elements move into the cable sheathing or the end sleeve with the consequence that the gripping elements are closed in a tong-like manner. Tissue specimens can be gripped and taken.

The following disadvantages have been recognized in the surgical gripping instruments art. When the index finger-middle finger hold is pulled back in the direction of the thumb hold, the thumb hold remains essentially stationary based on the normal coordination of fingers on the human hand whereas the index finger-middle finger hold is moved from its original position and towards the thumb. This means that as the index finger-middle finger hold approaches the thumb hold that the gripper, which is connected with the index finger-middle finger hold by way of the cable core, moves also in the direction of the thumb hold and away from the tissue specimen to be gripped.

However, it is frequently extremely difficult to adjust the gripping elements inside the body relative to the tissue specimen to be taken. Further, the region about the tissue specimen must be illuminated by way of light sources running parallel to the cable to observe the adjustment. Therefore it is undesirable if during the closing of the grippers this adjustment is lost again by a retracting motion of the gripping elements.

It is an objective of the invention to develop a surgical gripping instrument of the type mentioned above in such a way that, during the operation of the manual operating device by means of thumb and fingers in a manner corresponding to the natural motion of the human hand, the gripping elements do not change their position relative to the tissue spot to be gripped. In other words the closing motion of the gripping elements does not change the adjustment of the gripping elements relative to the tissue.

The solution according to the present invention is to firmly connect the thumb hold of the manual operating device with the end of the cable core on the operating side. The index finger-middle finger hold of the manual operating device is connected with the end of the cable sheathing on the operating side and is connected with the thumb hold through a direction reversing gear in such a way that, when the index finger-middle finger hold approaches the thumb hold, the cable sheathing moves in the direction of the gripping elements.

Furthermore, the invention affords a simple, low cost construction for the direction reversing gear which efficiently utilizes space. To meet this additional demand which is subordinate to the aforementioned problem, the direction reversing gear includes a pinion which is placed on a shaft connecting the thumb hold with the end of the cable core on the operating side. The index finger-middle finger hold is movable along this shaft. On the index finger-middle finger hold there is fastened a first rack element which meshes with the pinion. Extending lengthwise of the shaft is a second rack element which also meshes the pinion at a position diametrically opposite the first rack element. The second rack element is connected with a mounting for the end of the cable sheathing on the operating side.

An especially simple and space-saving construction results if the pinion is placed inside a recess in the shaft. The index finger-middle finger hold encloses the shaft which is movable within a shaft passage channel. Within the index finger-middle finger hold is a holding chamber for the rack element which is firmly fixed relative to the index finger-middle finger hold and is situated adjacent the shaft passage channel. Also adjacent the shaft passage channel within the index finger-middle finger hold is a guide channel for the second rack element which is movable relative to the index finger-middle finger hold.

In a well-known manner the thumb hold can be made as a ring which can be slid on the thumb up to the root of the thumb. The index finger-middle finger hold can be made as a spool-shaped roller body. The design of the thumb hold and the finger hold is conventional. Because the design of the holds is well known and the relative motion of the holds relative to each other in operation the same as conventional gripping instruments, a readapting of a person familiar with an old construction to a new manner of operation, is not necessary. Rather, the manner of operation remains entirely unchanged. However, the disadvantage of the previous construction is eliminated which was the fact that the gripping elements retracted from the tissue spot to be gripped. The device as defined in the invention can be used, for instance, in connection with grippers where the connection parts are made in one piece with the gripping elements and the gripping elements carry out a tong-like closing motion when the end of the cable sheathing or the end sleeve approach the connection parts.

BRIEF DESCRIPTION OF THE DRAWINGS

The sole FIGURE illustrates a preferred form of the gripping instrument according to the present invention and in a non-gripping mode.

DETAILED DESCRIPTION OF THE DRAWINGS

In the FIGURE a well-known tripodal gripping forceps construction is shown generally at 10 and incorporating the invention. These tripodal gripping forceps 10 are formed of three gripping elements 10a, 10b and 10c. These gripping elements 10a to 10c are joined through their connection parts 10aa, 10ba, and 10ca to the core 12 of the transmission cable 14 which extends within a sheathing 16. If the core 12 in the FIGURE is moved to the right, the gripping elements 10a to 10c through connection parts, 10aa, 10ba, and 10c are pulled into an end sleeve 18 of the cable sheathing 16 and are brought closer to each other in tong-like fashion.

The end of the transmission cable on the operating side is connected to a manual operating device indicated generally at 20. The operating device 20 includes a shaft 22 on whose end, toward the left in the FIGURE, the core 12 of the transmission cable 14 is firmly connected by means of a clamping screw 24. The shaft 22 carries on its right end a thumb hold in the form of a ring 6. An index finger-middle finger hold 28 moves along the length of the shaft 22 and has a shaft channel passage for guiding movement over the shaft. The index finger-middle finger hold 28 is made as a spool-shaped roller body. A recess 30 is provided in shaft 22 and a pinion 32 is placed in the recess and rotatable around an axis 34 extending through the shaft 22. In a holding chamber 35 of the index finger-middle finger hold 28 there is fastened by means of screws 40 a first rack element 38 which engages the pinion 32. Furthermore, within the index finger-middle finger hold 28 a guide channel 42 for a second rack element 44 is made. This second rack element carries on its end, which is on the left in the FIGURE, a mounting 46 for the end of the cable sheathing 16 on the operating side.

If the thumb hold 26 is held firmly, as in the vicinity of the thumb root, and the index finger-middle finger hold 28 brought closer to the thumb hold 26, the pinion 32 is moved in clockwise direction by the rack element 38 fixed with the index finger-middle finger hold 28. The consequence is that the second rack element 44 moves to the left in the FIGURE, together with the cable sheathing 16 and the end sleeve 18 as a result of which the gripping elements 10a to 10c go together in tong-like fashion. During that motion, a change of the position of the gripping elements 10a to 10c in the longitudinal direction of the transmission cable 14 does not take place since the gripping elements are firmly connected with the shaft 22 by way of the cable core 12 and thus shaft 22 is kept stationary by way of thumb hold 26.

I claim:

1. An improved surgical gripping instrument for introduction into body cavities of the type including a transmission cable having a sheathing at least partially along the length and a core with gripping elements at one end of the cable core, said gripping elements moving closer to each other in gripping, tong-like fashion upon extending the sheath over the gripping elements in a first direction toward the one cable end and a manual operating device including a finger hold and a thumb hold movable relative to each other, the improvement comprising:

first means fixedly securing the thumb hold to the cable core at a point spaced from the one cable core end; and reversing means connecting between the cable sheathing and the finger hold, said reversing means causing said sheathing to be moved in said first direction as said finger hold is moved opposite to the first direction and toward said thumb hold, whereby said one cable core end remains in a substantially constant position upon bringing the finger hold toward the thumb hold so that delicate adjustment of the gripping elements relative to a sample can be made.

2. An improved surgical gripping instrument according to claim 1 wherein said thumb hold has a shaft along which the finger hold is guided and said reversing means comprises a pinion on said shaft, a first rack associated with the finger hold and meshing with the pinion and a second rack meshing with the rack at a location diametrically opposite the first rack, said second rack being secured with the cable sheathing.

3. An improved surgical gripping instrument according to claim 1 wherein said thumb hold is configured as a ring which can be slid over a user's thumb.

4. An improved surgical gripping instrument according to claim 1 wherein said finger hold comprises a spool-shaped roller body.

5. An improved surgical gripping instrument according to claim 1 wherein said gripping elements and cable have a one-piece construction.

6. An improved surgical gripping instrument according to claim 2 wherein said shaft has a recess for reception of the pinion, said finger hold surrounds the shaft and has a channel for guiding movement of the finger hold along the shaft, and said finger hold defines a guide channel for the second rack.

* * * * *